United States Patent [19]

Jursich

[11] 3,959,358

[45] May 25, 1976

[54] POLYMERIZATION INHIBITION OF ACRYLATE ESTERS

[75] Inventor: Myron J. Jursich, Chicago, Ill.

[73] Assignee: Nalco Chemical Company, Oak Brook, Ill.

[22] Filed: Jan. 8, 1975

[21] Appl. No.: 539,219

[52] U.S. Cl............................................. 260/486 R
[51] Int. Cl.².......................................... C07C 69/54
[58] Field of Search ............................... 260/486 R

[56] References Cited
FOREIGN PATENTS OR APPLICATIONS 789,583  7/1968  Canada............................ 260/486 R Primary Examiner—Paul J. Killos
Attorney, Agent, or Firm—John G. Premo; Robert A. Miller; Barry W. Sufrin

[57] ABSTRACT

A new polymerization inhibitor combination has been developed which is effective in stabilizing acrylate esters during their distillation.

3 Claims, No Drawings

POLYMERIZATION INHIBITION OF ACRYLATE ESTERS

INTRODUCTION

Acrylate and methacrylate esters, which will be referred to herein simply as acrylate esters, provide a series of commercially useful monomers. These monomers are used in the production of numerous copolymers and homopolymers. In addition, monomeric acrylate esters serve as intermediates in a variety of chemical reactions.

In many of the applications in which monomeric acrylate esters are utilized, it is necessary to start with a relatively pure monomer. In order to obtain such pure monomers, it is often necessary to distill crude monomer mixtures obtained by such synthesis methods as the alcoholysis of acrylate esters.

Alcoholysis, which is also referred to as transesterification and ester interchange, involves the use of lower acrylate esters as starting materials for the preparation of other acrylate esters from alcohols of higher boiling points. The procedure involves the refluxing of the lower acrylate with the alcohol in the presence of catalyst and a polymerization inhibitor. More detailed descriptions of this method may be found in U.S. Pat. No. 2,138,763 and *Monomeric Acrylic Esters* by E. H. Riddle, Reinhold Publishing Corp., 1954, which are hereby incorporated by reference.

A significant problem which has been encountered during the distillation of the crude acrylate ester mixture is the unwanted formation of acrylate ester polymers. I have discovered a polymerization inhibitor combination which is effective in preventing such polymerization. My invention will be useful in the distillation of many different acrylate esters, including:

Methyl acrylate
Ethyl acrylate
Butyl acrylate
2-Ethylhexyl acrylate
Methyl methacrylate
Dimethylaminoethyl methacrylate
Ethyl methacrylate
Butyl methacrylate
Hexyl methacrylate
Decyl-octyl methacrylate
Lauryl methacrylate
Stearyl methacrylate Another benefit of my invention is the possible reuse or recycling of all inhibitor used during the distillation of acrylate esters. Since there is little or no polymer formed during the distillation of the crude acrylate ester mixture, the inhibitor may be extracted using a lower alkane or other solvent and separated from the insolubles remaining in the distillation pot.

THE INVENTION

The polymerization inhibitor combination which I have discovered is made up of a phenolic-type polymerization inhibitor and an amine-type polymerization inhibitor. The amount of the inhibitor combination used in the invention, based upon the weight of pure acrylate ester monomer present in the crude acrylate ester mixture, may vary between 0.01% and 20%, with a preferred concentration lying in the range of 1 to 10% and the most preferred concentration lying in the range of 2 to 6%.

The ratio of the phenolic-type inhibitor to the amine-type inhibitor will range from 4:1 to 1:4. The ratio in the preferred embodiment ranges between 2:1 and 1:2.

Phenol-type inhibitors effective in the invention include:
o-tert-butylphenol
p-methoxyphenol
2,6-di-tert-butyl-p-cresol
2,2'-methylenebis(6-tert-butyl-p-cresol)
4,4'-thiobis(6-tert-butyl-m-cresol)
4,4'-thiobis(6-tert-butyl-o-cresol)
thiobis(di-sec-amylphenol)
4,4'-butylidene(6-tert-butyl-m-cresol)
p,p'-biphenol
4,4'-methylenebis(2,6-di-tert-butylphenol)
1,5-naphthalenediol Amine-type inhibitors effective in the invention include:
N-phenyl-1-naphthylamine
N-phenyl-2-naphthylamine
N,N'-di-2-naphthyl-p-phenylenediamine
p-hydroxydiphenylamine
N,N'-diphenylphenylene diamine
7-amino-1-hydroxynaphthalene
4-nitrosodimethylaniline
phenylhydrazine
phenothiazine In particular, I have found that an inhibitor combination containing the phenolic-type polymerization inhibitor o-tert-butyl-phenol and the amine-type polymerization inhibitor N-phenyl-1-naphthylamine in the ratio of 3:1 to 1.5:1 is effective in preventing polymerization during the distillation of a crude N,N dialkyl substituted amino alkyl acrylate ester mixture where the concentration of the inhibitor combination, based upon the weight of pure acrylate ester present in the crude mixture, ranges between 3 and 6%.

PROPOSED THEORY

One possible explanation for the effectiveness of this inhibitor combination is based upon the assumption that the polymerization of acrylate esters during distillation is generated by both thermal activation and the action of polymerization initiating species like peroxides. I have found that phenol-type inhibitors satisfactorily prevent thermally activated polymerization when little or no oxygen is present. However, when oxygen is present, the phenol-type inhibitor alone is inadequate. Oxygen available during the distillation facilitates the formation of polymerization initiating peroxides and hydroperoxides; the phenol-type inhibitors alone cannot "scavenge" the oxygen present. The addition of the amine-type inhibitor, however, prevents peroxide initiated polymerization by: (1) directly scavenging oxygen, (2) rapidly reacting with initiating species generated by peroxide decomposition, or (3) terminating any free radicals formed.

EXAMPLES

Example 1

A 1 liter three-necked reaction flask was charged with 89 gm of dimethylethanol amine, 3.8 gm of ortho tertiary butyl phenol, 1 gm of LiOH.H$_2$O, and 85 gm of Skellysolve C, which is a commercial hydrocarbon mixture composed mainly of heptane. The reaction flask was equipped with a thermometer and a fractionator with distillation head and upright condenser attached.

The reaction mixture was heated to 95°C whereupon the Skellysolve was distilled overhead with small quantities of $H_2O$ and dimethylethanol amine. Since the latter was heavier and insoluble, it formed a layer at the bottom of the receiving vessel whereas the Skellysolve C formed an upper layer which could be returned to the flask after condensation. The total volume actually removed in the process was about 13 ml, 10 ml of hydrocarbon and 3 ml of lower layer consisting of about ⅔ dimethylethanol amine and ⅓ water. Overhead distillation temperature ranged from 70°–90°C. Following this water removal step, 125 gm of methyl methacrylate were added to the dry reaction mix and heated at 70°–80°C for at least one hour to form the ester interchange product, dimethylaminoethyl methacrylate and the byproduct methanol.

The temperature of the pot was then raised to about 85°–86°C at which time the binary of methanol and Skellysolve C were fractionally distilled. On condensation, the methanol formed a lower layer and the Skellysolve C formed an upper layer. The boiling point of the binary was 57°C. The remaining crude product was then distilled, as described in Example 2.

EXAMPLE 2

A 200 ml three-necked reaction flask was charged with about 94 gm of dimethylaminoethyl methacrylate and varying amounts of o-tert-butylphenol and N-phenol-1-naphthylamine, as indicated in Table I. The reaction flask was then equipped with a thermometer and a fractionator with distillation head and upright condenser attached and fitted with a vacuum dropping funnel so that as the distillation proceeded, more starting materials could be added to simulate a continuous distillation. The amount of material in the flask was kept at approximately 100 gm from the outset of the distillation to the very end when it was shut down. Occassionally, the unit would be shut down temporarily for the addition of more monomer to the funnel charging the pot.

Table I lists the percentages of insolubles formed, based upon the weight of dimethylaminoethyl methacrylate distilled. In runs 1 to 3 where the o-tert-butylphenol and N-phenyl-1-naphthylamine inhibitor combination was used, analysis of the insolubles indicated that no significant amounts of polymer were formed. In contrast to this, during runs 5 and 6, in which O-tert-butylphenol was used alone, polymer formation occurred.

Manufacturers of dimethylaminoethyl methacrylate generally do a double distillation to obtain high purity monomer. Using the o-tert-butylphenol and N-phenyl-1-naphthylamine combination, I was able to obtain, on a single distillation, dimethylaminoethyl methacrylate monomer with purities ranging from 92 to 100%, which is on a par with the double distillation commercial product.

Furthermore, I found that it was possible, using Skellysolve C or heptane, to extract the inhibitor combination and any monomeric dimethylaminoethyl methacrylate remaining in the distillation pot from the insolubles present. The Skellysolve extract containing inhibitor and monomer could then be recycled into the next reaction, resulting in the recovery of monomer left in the distillation pot as well as a reduction in material usage and process cost.

TABLE I

| | | | | DISTILLATION RESULTS | | | | |
|---|---|---|---|---|---|---|---|---|
| RUN | OTB (a) | NPA (a) | % INS./WT. DMAEM DISTILLED | % INS. DUE TO DISTILLATION* | INSOLUBLE ANALYSIS | DISTILLATION CONDITION(AV.) PT | HU | MM |
| 1 | 3.8 | 2(c) | 2.7 | 0.4 | (b) | 105.5 | 89 | 30–35 |
| 2 | 2.5 | 1.3 | 2.7 | 0.4 | (b) | 104.6 | 93 | 20–35 |
| 3 | 2.5 | 1.3 | ~ 3.0 | ~ 0.6 | (b) | 106.4 | 88 | 30–35 |
| 4 | 2.5 | 1.3 | 2.2 | 1.2 | — | 102 | 93 | 36–37 |
| 5 | 3.7 | — | > 6.3 | > 3.8 Est. | Polymer Present | 109 | 94 | 37–44 |
| 6** | 3.7 | — | 18 | 15.5 Est. | Polymer Present | 113 | 98 | 40–50 |

OTB = Ortho Tertiary Butyl Phenol
NPA = N-Phenyl-1-Naphthylamine
DMAEM = Dimethylaminoethyl Methacrylate
(a)% added based on theoretical yield of DMAEM
(b)Mainly a mixture of Li methacrylate and DMAEM methacrylate in varying ratios. Theoretical Li methacrylate that could form = 1.8%
(c)2% NPA was added to the continuous distillation pot at start of vacuum distillation of DMAEM
PT — Temperature of distillation pot (°C)
HT — Temperature of distillation head (°C)
MM — Millimeters pressure Hg.
INS. — Insolubles
*Total insolubles less insolubles present in crude
**Batch distillationn (rather than continuous)

I claim:
1. A method for inhibiting the polymerization of crude dimethylaminoethyl methacrylate during its purification by distillation which comprises conducting said distillation in the presence of an inhibitor combination consisting essentially of a phenolictype polymerization inhibitor selected from the group consisting of: o-tert-butylphenol, p-methoxyphenol, 2,6-di-tert-butyl-p-cresol, 2,2'-methylenebis (6-tert-butyl-p-cresol), 4,4'λ thiobis (6-tert-butyl-m-cresol, 4,4'-thiobis (6-tert-butyl-o-cresol), thiobis (di-sec-amylphenol), 4,4'-butylidene (6-tert-butyl-m-cresol), p,p'-biphenol, 4,4'-methylenebis (2,6-di-tert-butylphenol) and 1,5-naphthalenediol, and an amine-type polymerization inhibitor selected from the group consisting of: N-phenyl-1-naphthylamine, N,N'-di-2-naphthyl-p-phenylenediamine, and 7-amino-1-hydroxynaphthalene combined in a weight ratio of 4:1 to 1:4 with the amount of the inhibitor combination being 0.01 to 20% by weight, based on the weight of the pure acrylate ester present in the crude acrylate ester mixture.

2. The method of claim 1 wherein the amount of the inhibitor combination is 1 to 10% by weight, based on the weight of the pure dimethylaminoethyl methacrylate present in the crude dimethylaminoethyl methacrylate mixture.

3. A polymerization inhibition combination for preventing the polymerization of dimethylaminoethyl methacrylate during purification by distillation and storage consisting essentially of a phenolic-type inhibitor selected from the group consisting of: o-tert-butylphenol, p-methoxyphenol, 2,6-di-tert-butyl-p-cresol, 2,2'-methylenebis (6-tert-butyl-p-cresol), 4,4'thiobis (6-tert-butyl-m-cresol, 4,4'-thiobis (6-tert-butyl-o-cresol), thiobis (di-sec-amylphenol), 4,4'-butylidene (6-tert-butyl-m-cresol), p,p'-biphenol, 4,4'-methylenebis (2,6-di-tert-butylphenol) and 1,5-naphthalenediol, and an amine-type inhibitor selected from the group consisting of: N-phenyl-1-naphthylamine, N,N'-di-2-naphthyl-p-phenylenediamine, and 7-amino-1-hydroxy-naphthalene in the ratio of 4:1 to 1:4.

* * * * *